United States Patent
Basu et al.

(10) Patent No.: US 9,086,361 B2
(45) Date of Patent: Jul. 21, 2015

(54) DETECTOR DEVICE, INSPECTION APPARATUS AND METHOD

(75) Inventors: Arnab Basu, Belmont (GB); Ian Radley, Bishop Auckland Durham (GB); Max Robinson, Shincliffe (GB)

(73) Assignee: Kromek Limited, Sedgefield, Durham (GB)

( * ) Notice: Subject to any disclaimer, the term of this patent is extended or adjusted under 35 U.S.C. 154(b) by 324 days.

(21) Appl. No.: 13/581,427

(22) PCT Filed: Mar. 11, 2011

(86) PCT No.: PCT/GB2011/050483
§ 371 (c)(1),
(2), (4) Date: Nov. 7, 2012

(87) PCT Pub. No.: WO2011/110862
PCT Pub. Date: Sep. 15, 2011

(65) Prior Publication Data
US 2013/0051521 A1    Feb. 28, 2013

(30) Foreign Application Priority Data
Mar. 12, 2010    (GB) .................................. 1004121.8

(51) Int. Cl.
*G01N 23/00* (2006.01)
*G01N 23/087* (2006.01)

(52) U.S. Cl.
CPC .................................... *G01N 23/087* (2013.01)

(58) Field of Classification Search
USPC ......................................................... 378/53
See application file for complete search history.

(56) References Cited

U.S. PATENT DOCUMENTS

| 4,361,900 A | * | 11/1982 | Siedband ........................ 378/98 |
| 4,626,688 A | | 12/1986 | Barnes |
| 4,843,619 A | * | 6/1989 | Sheridan ........................ 378/207 |
| 5,285,489 A | | 2/1994 | Ohtsuchi et al. |

(Continued)

FOREIGN PATENT DOCUMENTS

| EP | 0 365 203 | 4/1990 |
| EP | 1 063 538 | 12/2000 |

(Continued)

OTHER PUBLICATIONS

Kelcz F. et al., "Absorption-edge fluoroscopy using a three-spectrum technique", Medical Physics 3(3):159-168 (May/Jun. 1976).*

(Continued)

*Primary Examiner* — Phillip A Johnston
(74) *Attorney, Agent, or Firm* — Drinker Biddle & Reath LLP

(57) ABSTRACT

A detector device is described comprising an x-ray detector structure having a detection surface defining at least one separately addressable region for detecting incident x-ray radiation intensity thereon, wherein the separately addressable region is divided into a plurality of sub-regions provided on the detection surface each provided with a filter layer on the detection surface, the filter layers of a given separately addressable region comprising discrete and different materials with discrete defined and spectroscopically spaced x-ray absorption edges. A method of device manufacture, and an apparatus and method for the inspection and characterization of materials employing such a detector device, are also described.

24 Claims, 1 Drawing Sheet

(56) References Cited

U.S. PATENT DOCUMENTS

| | | | |
|---|---|---|---|
| 5,943,388 A | 8/1999 | Turner | |
| 6,285,029 B1 | 9/2001 | Shahar et al. | |
| 8,111,803 B2 * | 2/2012 | Edic et al. | 378/5 |
| 2005/0259783 A1 * | 11/2005 | Hoffman | 378/19 |
| 2011/0194668 A1 | 8/2011 | Kanno | |

FOREIGN PATENT DOCUMENTS

| | | |
|---|---|---|
| GB | 2 244 328 | 11/1991 |
| GB | 2 289 983 | 12/1995 |
| JP | 4130292 A | 5/1992 |
| JP | 527043 | 2/1993 |
| JP | 6121791 | 5/1994 |
| JP | 8289886 | 11/1996 |
| JP | 200771602 A | 3/2007 |
| WO | WO 2008/142446 A2 | 11/2008 |
| WO | 2009022625 A1 | 2/2009 |
| WO | WO 2010/058201 A2 | 5/2010 |

OTHER PUBLICATIONS

International Search Report and Written Opinion, pp. 10, Jun. 7, 2011.

Japanese Office Action, Notice of Reasons for Rejection, Jan. 13, 2015, 7 pgs.

* cited by examiner

DETECTOR DEVICE, INSPECTION APPARATUS AND METHOD

FIELD OF THE INVENTION

The invention relates to a detector device and its manufacture, and to an apparatus and method for the inspection and characterisation of materials employing such a detector device.

The invention in particular relates to a detector device, apparatus and method making use of high-energy radiation, in particular x-rays, to scan objects where it is desirable to gain information about their internal structure and composition. This principle may be employed for example for the characterisation or testing of structures for quality control purposes or the purposes of determining the integrity of the structure, or the like, for example in the field of electronic devices, although the invention is not limited to such a field of application.

The invention in particular relates especially to an apparatus and method that operates by or in conjunction with the generation of an image, but is not limited to such imaging.

BACKGROUND

The attenuation of transmitted x-rays incident upon and emergent from an object, in particular as attributable to photoelectric absorption, has been used as the basis for screening objects to obtain some form of representational data representative of the contents or components thereof relative to each other, and for example to generate an image.

The data can give information at various levels. Even if intensity data is collected monochromatically across a broad spectrum, attenuation is known to vary both with the thickness/density of an object. By use of suitable detectors and a suitable source, radiographs of an item under test in the form of images based on the absorption behaviour of an object or its contents or components can be generated.

This method tends to give limited information about the material content. In essence, at its simplest, all that is being measured is transmissivity of the object to the source radiation. The detector merely collects amplitude information, and does not discriminate transmitted radiation spectroscopically.

However, it is known that spectroscopic information from transmitted x-rays could be used to give additional information about the material content of the objects or components being scanned. It is known that the x-ray absorption properties of any material can vary spectroscopically with incident x-ray photon frequency/energy, and that this effect depends in particular on atomic number. This has led to development of dual-band or dual-energy detectors which are capable of separately identifying low- and high-energy bands from the spectrum of x-ray emissions of a suitable source. Such detectors are described for example in U.S. Pat. No. 4,626,688.

A dual-energy system thus confers some limited information about composition. For example, a very crude approximation can be made that organic materials tend to be in the former category and most inorganic materials in the latter category, and a or dual-energy detector can thus make an approximate organic/inorganic discrimination. However the organic/inorganic division is crude and approximate. Conventional dual-energy detectors give limited real spectroscopic information about the spectrum of transmitted x-rays.

Multiple sources and/or filters and/or detector arrays can be used to produce a system with the ability to resolve into further bands across a source spectrum even if individual detectors are inherently monochromatic or dual-energy.

Recent development of detectors that can resolve spectroscopic information about the transmitted x-rays more effectively has led to the development of apparatus that inherently simultaneously discriminates across a larger range plurality of energy bands, for example to generate multispectral images. For example U.S. Pat. No. 5,943,388 describes a system that makes use of the inherent ability of cadmium telluride detectors to resolve incident x-rays spectroscopically across a broad spectrum to produce intensity data across at least three energy bands simultaneously and generate at least three images. This better exploits the effect of differential spectral absorption by different materials and better approximates transmissivity to composition but is still limited to the information that can be conveyed by a displayed image, and by the approximate and indicative nature of any relationship between colour on a multispectral image, especially based on relatively wide energy bands, and composition of material in the transmission path.

If it is additionally desirable to generate specific compositional information from a spectroscopically resolved intensity dataset, and in particular to supplement that available by plural band imaging alone, the intensity data may further be numerically processed to fit the measured spectroscopically resolved intensity to known relationships for x-ray attenuation, for example with reference to the incident spectrum. An example of such an analysis is described in WO2008/142446.

Such techniques can be very powerful, particularly in applications where it is desired to gain accurate materials characterisation from objects comprising multiple component materials, such as airline luggage, in order to identify with precision particular to compositions of matter, for example comprising high molecular weight organics, which may be indicative of the presence of contraband materials in the luggage. However, because of the fine compositional distinctions which it is necessary to make in such applications, and the complexity of calculations that may therefore be involved in fitting intensity data to appropriate numerical relationships, the method can be relatively time consuming and can test the resolution limit of the detector material.

An alternative approach, which does not involved such degree of numerical analysis, might be preferable where it is desirable to develop a detector device, apparatus and method for the inspection and characterisation of materials in other situations, for example where such complex and close material distinctions need not be made and/or where a high throughput rate is desired.

SUMMARY OF THE INVENTION

Thus, in accordance with the invention in a first aspect, a detector device comprises an x-ray detector structure having a detection surface defining at least one separately addressable region for detecting incident x-ray radiation intensity thereon, wherein the separately addressable region is divided into a plurality of sub-regions provided on the detection surface each provided with a filter layer on the detection surface, the filter layers of a given separately addressable region comprising discrete and different materials with discrete defined and spectroscopically spaced x-ray absorption edges.

A detector embodying the principles of the invention in its first aspect is thus adapted to make use of information across the breadth of a relatively broad x-ray spectrum in order to derive information about the x-ray transmission behaviour of an object under test when it is suitably placed in a scanning zone between a detector and a suitable source spaced therefrom. However, it does not seek to do this by resolving intensity information across the entire spectrum and by fitting this fully spectroscopcially resolved intensity to known relationships in order to determine material composition in detail. Instead, each separately addressable region of the detector surface into a plurality of sub-regions each with filters exhibiting different and specifically characteristic x-ray absorption edges from which separate and district intensity readings may be obtained. This enables the detector to identify, quickly and effectively, equivalent characteristic absorption edges in a material under test.

Such a detector makes possible a particularly rapid identification of metallic elements such as cooper, gold and tin, without requiring a detailed numerical analysis of the full absorption spectrum. The x-ray transmission behaviour of these elements and of other pure elements shows a classic effect where the energy of the x-ray photons is equal to the energy required to eject an electron from a particular electronic shell. At such energy, there is a very sharp and distinct rise in the attenuation co-efficient which is characteristic of that element. This represents an x-ray absorption edge for that element.

Of particular interest in accordance with the invention is this effect as observed when electrons are rejected from the K-shell of the atom. This produces a particular distinct rise in the attenuation co-efficient, referred to as the K-absorption edge, and the values of this characteristic absorption edge for all elements are very well tabulated. Thus, in the preferred case, at least some of the filter layers of a given separately addressable region are selected to have discrete defined and spectroscopically spaced K-edges.

The essence of the invention is to exploit this effect to provide a detector which is able rapidly to discriminate between a small number of discrete target materials with distinctive absorption edges, and in particular a small number of elemental materials. Such a detector will find particular application where an object under test, or at least the critical parts thereof, are known to consist of such a relatively small number of discrete materials. Such a detector might for example find application in the x-ray inspection of electronic devices and circuits. Each filter layer comprises one or more target elemental materials selected from the group of materials that the device is intended to enable to be rapidly identified/discriminated. Having regard to the preferred application set out above, the filter material may be selected from a group including nickel, copper, silver, tin and gold in particular.

In accordance with the principles of the invention, the materials that will be chosen for the filters will be selected to have distinct absorption edges, and in particular distinct K-absorption edges, and will be selected from the group of materials that the device is intended to enable to be rapidly identified/discriminated. Ideally, materials should have a distinct absorption edge both in the sense that the edge itself represents a distinct discontinuity in absorption co-efficient, and in the sense that different materials have absorption edges spaced a substantial distance apart in terms of photon energy so as to cover a substantial part of the x-ray spectrum of the source. In relation to the elements of interest in the preferred application, the K-absorption edge is particularly distinctive. Typically, the materials will be selected to act as K-edge filters. Preferably, the material of the filter will be selected to exhibit a K-edged discontinuity in the absorption co-efficient with a ratio of at least 5 to 1. It may be as high as at least 10 to 1 or even 100 to 1.

In a simplest embodiment, each filter may comprise a substantial pure elemental material, for example selected from the above list. Discrete filters are provided to define at least two sub-regions of each separately addressable region, and in a preferred case at least three. The discrete filters are chosen to have distinct absorption edges spaced across the spectrum of the source and selected from the materials which are expected to be present in a target object under test, and which it is intended the detector will discriminate between.

If, for example, a region consisted of two sub-regions a filter material may be chosen from a lower and a higher end of the energy spectrum of the source. If, for example, a region consisted of three sub-regions, separate filter materials could be selected, with reference to a particular target material with a particular characteristic edge of interest, with a filter having a characteristic absorption edge below the edge of interest, a filter having a characteristic absorption edge above the edge of interest, and a filter having an absorption edge with the edge of interest.

In principle, a comparison of the intensities detected in each sub-region of a given region, based on a determination of whether the same x-ray signal is produced in all the sub-regions or not, can be used to determine the presence or absence of a particular edge in the incident intensity at that region and hence the presence or absence of a material having the particular characteristic absorption edge in an object under test. This result can be obtained merely by comparing the intensity measured at each of the plural sub-region simultaneously, and merely from inferences drawn about the edge, without being limited by the inherent limitations of the energy resolution of the underlying detector.

To achieve this effect, the detector may further comprise or be adapted for use with a comparator to compare intensity at each of the sub-regions of a given separately addressable region and produce therefrom in use an indication of the presence or otherwise of a material having a particular absorption edge in an object under test based on a determination of whether the same x-ray signal is produced in all the sub-regions Each sub-region comprises a filter material having at least one defined and predetermined characteristic absorption edge, and in particular at least one particular defined and predetermined K-absorption edge, with different filter materials being used for different sub-regions in a given separately addressable region to define sub-regions with particular and different characteristic absorption edges spaced apart across the spectrum of the source, and selected with reference expected target materials. In a simplest embodiment, each filter material may be selected to consist of a single substantially pure element, in particular so as to give a particularly marked and pre-selected K-absorption edge. In an alternative embodiment, a given filter material may consist of more than one element, selected to define plural distinct K-absorption edges, so that a sub-region with such a filter would define a very specific part of the spectrum transmitted. Additionally or alternatively such multiple elements may be incorporated by providing more than three sub regions in a given separately addressable region of the detector surface. If these are chosen carefully then the separately addressable region as a whole would become even more specific in terms of material identification.

A detector in accordance with the invention may comprise a single separately addressable region subdivided into plural discrete sub-regions carrying discrete filter materials (and themselves individually addressable so that separate intensity readings may be collected for each). However, for many practical applications it will be desirable for a detector system to define in familiar manner a detection space which is divided into a plurality of discrete areas for example in linear or area array. Conveniently, this may be achieved in that the detector system defines a plurality of separately addressable regions in particular disposed in such a linear or area array.

A detector in accordance with the general principles of the invention is readily adaptable in accordance with such principles. For example, the detector structure of the invention may comprise a single element defining plural separately addressable regions and/or may comprise plural detector elements in a linear or area array each of which detector element defines single or plural separately addressable regions. In accordance with the invention at least some of such plural separately addressable regions are divided into discrete sub-regions by provision of discrete filter materials in the manner above described.

Additionally or alternatively a detector system may define a detection space having plural such discrete regions by adaptation to perform a suitable raster scan by appropriate movement of detector elements and/or radiation source, for example in the manner described in PCT/GB2009/051541.

The sub-division of the detection space into plural discrete areas (either by provision of separately addressable regions on the detector or otherwise), for example into a linear or area array, finds particular application in relation to imaging. In such an application such discrete areas may commonly be referred to as pixels. The present invention is suitable for use in imaging applications, but is not limited to such applications. Accordingly, where reference is made herein to imaging applications it will be understood that these are by way of example, and the skilled person will appreciate that the terms pixel/super pixel/separately addressable region and the terms sub-pixel/sub-region are essentially used interchangeably.

It ought to be appreciated that a detector in accordance with the broad principles of the invention is enabled to exploit the spectrum of a broad spectrum source by means of provision of appropriately selected filter materials, in particular as K-edge filters, and is thus enabled to discriminate at least to some extent between different parts of the broad spectrum of the source. The detector structure itself may therefore be a monochromatic broad spectrum detector, and need not itself (that is, need not inherently otherwise than by provision of filters) be capable of resolving incident radiation further spectroscopically.

However, in a possible embodiment, the detector structure is additionally itself adapted to resolve incident radiation spectroscopically across a plurality of energy bands within the spectrum of the source, and preferably across at least three energy bands within the spectrum of the source. The detector structure is adapted to resolve incident radiation spectroscopically in the sense that it is adapted to differentiate incident radiation simultaneously into plural separate energy bands across the spectrum of the source. For example, the detector structure exhibits a spectroscopically variable response across at least a part of the source spectrum allowing such simultaneous differentiation of incident radiation into plural energy bands. Preferably, the detector structure may be adapted to produce spectroscopic resolution in that it exhibits a direct spectroscopic response.

In all such cases, the ability to differentiate incident radiation simultaneously into plural separate energy bands across the spectrum of the source may be obtained by provision of a single material structure or by provision of a multiple component detector structure with suitable properties. In a particular preferred case a detector structure is fabricated from a material selected to exhibit inherently as a direct material property a direct variable electrical and for example photoelectric response to different parts of the source spectrum.

For example, the detector systems or elements comprise a semiconductor material or materials preferably formed as a bulk crystal, and for example as a bulk single crystal (where bulk crystal in this context indicates a thickness of at least 500 µm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where $a+b<1$ and a and/or b may be zero.

The detector of the invention is adapted, at least by provision of the discrete filters on the detector surface, to be used with a broad spectrum x-ray radiation source capable of producing broad spectrum emission over a range of energies. For example the said spectrum may comprise at least one or more parts of the range 120 eV to 1 MeV, and more particularly at least a part, and for example a major part, of the range 1 keV to 160 keV or of the range 5 keV to 100 keV. Notably, the first such range encompasses the K-edges of elements 11 to 103 and the second such range encompasses the K-edges of nickel, copper, silver, tin and gold, which are particular target materials in a useful application of the invention to the inspection of electronic devices.

Filter materials are selected to exhibit characteristic absorption edges spaced apart across this emission spectrum, and in particular preferably spread across at least a major part of this emission spectrum. In the case where the detector structure is itself additionally adapted to produce spectroscopic resolution, it is similarly preferably so adapted across at least a major part of this emission spectrum.

In a further aspect of the invention, a method of production of a detector comprises the steps of:

providing an x-ray detector structure and defining at least one separately addressable region on a detection surface thereof for detecting incident x-ray radiation intensity thereon in use;

depositing on the detection surface of each separately addressable region a plurality of discrete filter layers each defining a sub-region on the detection surface, the filter layers of a given separately addressable region comprising discrete and different materials with discrete defined and spectroscopically spaced x-ray absorption edges.

The method is thus a method of producing the device of the first aspect of the invention, and further preferred features will be understood by analogy with those described for the first aspect of the invention.

In a third aspect of the invention, an apparatus for the inspection and characterisation of materials comprises:

a detector system composed of at least one detector device in accordance with the first aspect of the invention or fabricated in accordance with the method of the second aspect of the invention;

an x-ray source spaced therefrom to define an object scanning zone therebetween.

In use, an object to be inspected is brought into the scanning zone, for example placed in the stationary position for a static scan or moved through the scanning zone to provide a moving scan. Radiation from the x-ray source is caused to impinge upon the object. The detector system is suitably positioned, remotely spaced from the x-ray source and juxtaposed to the object under test, so as to collect emergent radiation which has been transmitted through the object.

The principles of the detector above described are employed. In particular its ability to identify, by appropriate selection of filter materials and especially in cases where a relatively limited number of target materials are expected in the object under test, characteristic absorption edges from the transmitted radiation, enables inferences to be drawn about the material composition in the transmitted data in simple manner without requiring numerical analysis across the entire spectrum of the source and without the usual limitations of the resolution of the detector structure itself.

By analogy in a fourth aspect of the invention, a method for the inspection and characterisation of materials comprises:

providing a detector system composed of at least one detector device in accordance with the first aspect of the invention or fabricated in accordance with the method of the second aspect of the invention;

providing an x-ray source spaced therefrom to define an object scanning zone therebetween;

irradiating an object under test in the scanning zone;

comparing incident intensity from each sub-region of a separately addressable region of the detector;

drawing inferences therefrom on the presence or absence of particular absorption edges in the material of the object under test, and hence about composition.

The radiation source should be capable of generating a sufficiently broad spectrum of radiation to enable the exploitation of the principles of the invention. The source should generate a sufficiently broad spectrum to cover typical absorption edges, and especially K-absorption edges, of likely target materials. The source may be a single broad spectrum source across a sufficiently broad spectrum. Alternatively the source may be a plural source comprising a combination of sources at different energies to provide the necessary total spectrum spread.

Preferably the source generates radiation across at least one or more parts of the range of 120 eV to 1 MeV, and more preferably across at least a part, and for example a major part, of the range 1 keV to 160 keV or of the range 5 keV to 100 keV. Notably, the first such range encompasses the K-edges of elements 11 to 103 and the second such range encompasses the K-edges of nickel, copper, silver, tin and gold, which are particular target materials in a useful application of the invention to the inspection of electronic devices.

A collimator may be provided to produce an emitted beam of suitable geometry from the source. The geometry of the emitted beam will determine the most useful geometry of the detector system. No particular beam geometry is mandated.

The apparatus and method of the invention may be adapted to produce scans of stationary objects or of objects moving through the scanning zone.

In a possible embodiment of the first case the method thus comprises placing a sample under test in the scanning zone and supporting it in the scanning zone on an object holder and the apparatus comprises such object holder. In a possible embodiment of the second case information is collected regarding the transmissivity of an object under test in the scanning zone in a plurality of scanning positions between which the object is translated and/or rotated. In accordance with this embodiment the method comprises the additional step of causing an object to move relative to and for example through the scanning zone as a plurality of successive datasets of information about radiation incident at the detector are collected. In accordance with this embodiment the apparatus comprises a suitable object conveyor adapted to cause the object so to move in use.

At its most basic, the invention enables inferences to be drawn about the presence or absence of particular absorption edges in a target material, and hence about composition. It is not necessary to generate an image to do this. However, the invention does not exclude the possibility that the invention forms part of and supplements the information offered by a scanning imaging system, and indeed is readily adapted to such a system.

Preferably, the method further comprises the generation of an image from transmitted intensity data. The image is preferably an image including a representation of the inferences drawn from comparison of the intensity data from each sub-region of each separately addressable region (which in this context may be considered each sub-pixel of each pixel on the detector surface). That is, an image is generated in which each separately addressable region comprises an image pixel and in which the image includes a representation of the inferences drawn from comparison of the intensity data from each sub-region. For example, different identified absorption edge response may be represented as different colours and/or intensities and/or hues. The apparatus preferably comprises an imaging module to generate such images from the intensity data collected at the detector.

Additionally or alternatively in the preferred case where the detector structure inherently resolves the source spectrum into a plurality of frequency bands within the spectrum of the source, an image may be produced which is resolved spectroscopically across a plurality of frequency bands within the spectrum of the source which are allocated to generate a series of energy-differentiated images in accordance with conventional principles. The apparatus preferably comprises an imaging module to generate images based on the plural energy-resolved datasets, and in particular to generate such combination images.

The method of the invention conveniently further provides the additional step of displaying such generated image or images, and in the case of multiple images might involve displaying such images simultaneously or sequentially. The apparatus preferably comprises a suitable image display.

The method of the invention conveniently further provides the additional step of displaying such generated image or images, and in the case of multiple images might involve displaying such images simultaneously or sequentially.

For clarification it should be understood that where used herein a reference to the generation of image is a reference to the creation of information dataset, for example in the form of a suitable stored and manipulatable data file, from which a visual representation of the underlying structure of the object under investigation could be produced, and references to displaying this image are references to presenting an image generated from such a dataset in a visually accessible form, for example on a suitable display means.

BRIEF DESCRIPTION OF THE DRAWINGS

The invention will now be described by way of example only with reference to FIGS. 1 and 2 of the accompanying drawings in which.

DESCRIPTION OF THE PREFERRED EMBODIMENTS

Figure 1:
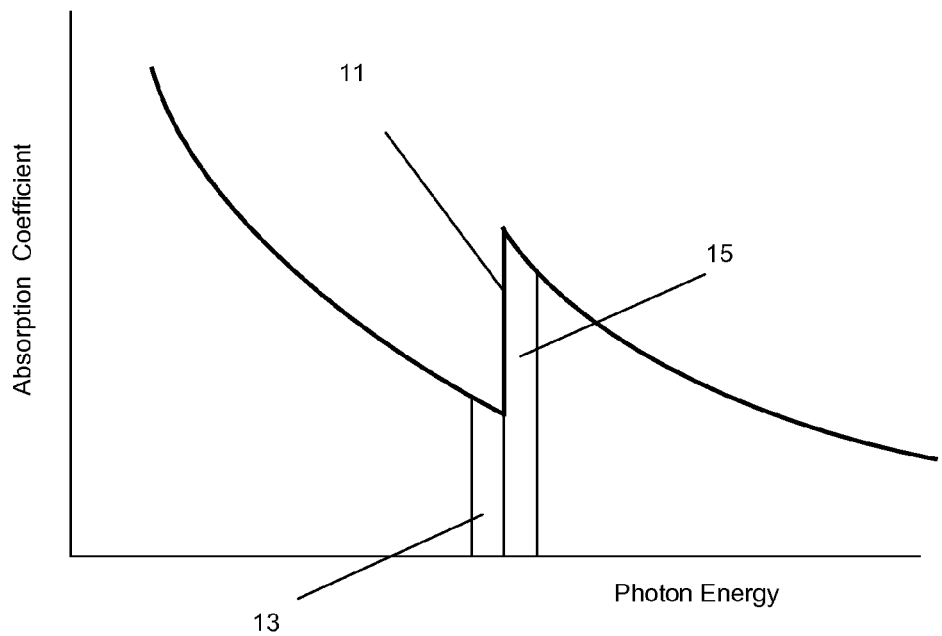
FIG. 1 is a general schematic of a characteristic absorption edge of an elemental material.

FIG. 1 illustrates in general schematic form a typical plot of absorption co-efficient versus photon energy for an elemental material, to illustrate schematically the presence of an absorption edge. Only a single edge 11 is shown for clarity. This edge might for example be the K-edge. The graph is not scaled, as the position of this edge varies with photon energy from element to element.

It is well established that for a given element, the overall tenancy for the x-ray absorption co-efficient to decrease with increasing energy of the incident x-ray photon is qualified by a very sharp and distinct rise which is characteristic of the material at a point where the energy of the photon is equal to that of the binding energy of an electron in one of the shells of the atom. Of particular interest here is this effect as observed when electrons are rejected from the K-shell of the atom. This edge is referred to as the K-absorption edge.

Both the general shape of curve in FIG. 1 and the characteristic edges such as the K-edge 11 are specifically characteristic of the element in question. It is therefore in principle possible, as has been explored in some of the prior art referenced above, to resolve a transmitted radiation spectrum of emergent radiation from a scanned object spectroscopically across the full breadth of photon energies and, by various numerical analysis techniques, to fit this data to known relationships for various different compositional components, and to obtain detailed information about the composition of an object under scan. However, the numerical analysis techniques required can be complex, and can require high detector resolutions.

An alternative approach can be suggested for identifying specific elemental components in particular, which is based on the characteristic energy of the edge 11 alone. This is basis of the present invention.

The K-edge is of elements are very well tabulated, and in particular the K-edges of the metallic elements which are of particular interest in relation to electronic components have been presented in table 1.

As can be observed from FIG. 1, the absorption edge is characterised by a substantial difference between a region of relatively low absorption 13 just below the edge (in terms of photon energy), and a region of relatively high absorption 15 just above it. This difference gives a way of identifying an elemental material, by identifying presence or absence of the edge in radiation transmitted through a material under test, that does not require particular numerical methods or a particularly high resolution for the detector. It is this principle which is exploited in accordance with the invention.

TABLE 1

| K-edges of Selected Metallic Elements | |
|---|---|
| Element | K-edge (keV) |
| Nickel | 8.339 |
| Copper | 8.993 |
| Silver | 25.531 |
| Tin | 29.251 |
| Gold | 80.729 |

Figure 2:
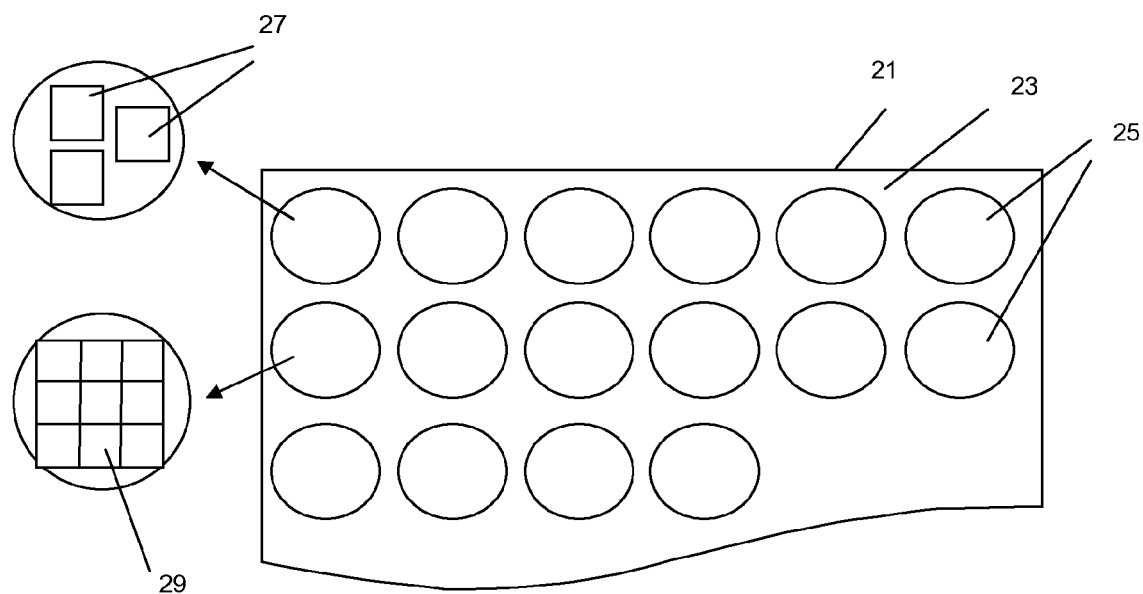
FIG. 2 is an illustration in plan view of a possible arrangement of pixelated filters on a detector embodying the principles of the invention.

A detector embodying the principles of the invention is illustrated in FIG. 2. The detector comprises a detector structure capable of detecting incident x-rays after transmission through an object. The detector structure may do this inherently via a photoelectric interaction within the material, or via provision of multiple layers, for example in that it includes a scintillator layer generating photons of other energy in response to incident x-ray photons and a detector layer to detect those secondary photons. In a preferred case the detector inherently detects x-ray photons, and in particular in a manner which allows them to be resolved spectroscopically, and is for example of cadmium telluride or like material.

The surface of the detector is divided into plural pixels. Each pixel is separately addressable so as to enable collection for each pixel of a discrete dataset of incident intensity information. A pixel may be defined as a discrete detector element, or, as is in the illustrated embodiment, may be defined virtually as a region on the surface and separately addressed by suitable control electronics. In the embodiment, plural pixels 25 are shown in two dimensional array on the surface 23 of the detector 21. The precise shape, size and distribution of pixels will vary dependent upon the application.

In accordance with the principles of the invention, each pixel is sub-divided into plurality of sub-pixels. Each sub-pixel is provided with a filter layer comprising a material selected to have at least one particularly characteristic absorption edge. In principle, meaningful information can be obtained merely be dividing a pixel into two sub-pixels, but preferably each pixel is sub-divided, as in the upper alternative on FIG. 2, into at least three sub-pixels 27. A greater number of sub-pixels, for example the array of nine 29 also illustrated in the lower alternative on FIG. 2, each of a different filter material, would give a more powerful resolution.

The detector is particularly adapted to be used where a target object to be tested is, or at least the critical components thereof are, known to consist of a relatively small number of identified elements. The principle of the invention is that each sub-pixel will be coated with a K-edge filter that is chosen from the group that is required to be rapidly identified. For example, it may be desirable to identify one or more of nickel, copper, silver, tin and gold components. In those circumstances, these materials will also be used for the filters. It can be seen, in the above example, that if a pixel consists of three sub-pixels, a different material could be picked for each filter from those listed in Table 1. Inferences can then be drawn depending upon whether the same x-ray signal appears on all three sub-pixels, one with a filter below the edge of interest, one with a filter above the edge of interest, and the third having filter at the edge of interest. This can be determined without complex calculations and without the limitations of the energy resolution of the detector.

In a simple embodiment each of the sub-pixels is defined by a filter comprising just one of the indicated elements. Alternatively, it might be possible to use a filter consisting of more than one element, for example as a mixture or in multiple layers.

In a simple embodiment a filter is used to define an edge. Additionally, in the preferred case where a spectroscopically resolving detector is used such as the CdTe detector in the example embodiment, this characteristic may be used supplementarily. The multi-spectral characteristics of CdTe type detectors could be used to determine the lower energy edge of the low absorption region (13) and/or the upper energy edge of the high absorption region (15). This might have particular use when more than one filter is used on a particular pixel, it would have the effect of better defining the limits of the various filtered energy regions.

The invention claimed is:

1. A detector device comprising an x-ray detector structure having a detection surface defining a plurality of separately addressable regions disposed in an area array for detecting incident x-ray radiation intensity thereon, wherein the separately addressable region is divided into a plurality of sub-regions provided spaced across the detection surface of the separately addressable region, each sub-region provided with a filter layer on the detection surface, the filter layers of each sub-region of a given separately addressable region comprising discrete and different materials with discrete defined and spectroscopically spaced x-ray absorption edges, whereby each separately addressable region is divided into at least three sub-regions, wherein each region includes a filter layer selected with reference to a target material with a particular characteristic edge of interest such as to comprise a filter layer having a characteristic absorption edge below the edge of interest, a filter layer having a characteristic absorption edge above the edge of interest, and a filter layer having an absorption edge with the edge of interest, and wherein the detector structure is itself adapted to resolve incident radiation spectroscopically simultaneously across at least three energy bands within the spectrum of a source.

2. A detector in accordance with claim 1 wherein the filter layers of a given separately addressable region are selected to have discrete defined and spectroscopically spaced K-edges.

3. A detector in accordance with claim 1 wherein each filter layer comprises one or more target elemental materials selected from the group of materials that the device is intended to enable to be rapidly identified and/or discriminated.

4. A detector in accordance with claim 1 wherein each filter layer comprises one or more target materials selected from the group comprising nickel, copper, silver, tin and gold.

5. A detector in accordance with claim 1 wherein each filter layer comprises a single substantially pure elemental material.

6. A detector in accordance with claim 1 wherein the separately addressable region is divided into at least two sub-regions in that it comprises at least two filter layers respectively selected to exhibit an absorption edge at a lower and a higher end of the energy spectrum of an intended source.

7. A detector in accordance with claim 1 further comprising a comparator to compare intensity at each of the sub-regions of a given separately addressable region and produce therefrom in use an indication of the presence or otherwise of a material having a particular absorption edge in an object under test based on a determination of whether the same x-ray signal is produced in all the sub-regions.

8. A detector in accordance with claim 1 comprising a plurality of separately addressable regions disposed across the detector surface, at least some of which are subdivided into plural discrete sub-regions.

9. A detector in accordance with claim 8 wherein a structurally discrete detector element is adapted to define a plurality of separately addressable regions.

10. A detector in accordance with claim 8 wherein a plurality of structurally discrete detector elements is provided, each adapted to define at least one separately addressable region.

11. A detector in accordance with claim 1 wherein the detector structure is adapted to produce spectroscopic resolution in that it is fabricated from a material selected to exhibit inherently as a direct material property a direct variable electrical response to different parts of the source spectrum.

12. A detector in accordance with claim 11 wherein the semiconductor material is selected from cadmium telluride, cadmium zinc telluride (CZT), cadmium manganese telluride (CMT), germanium, lanthanum bromide, and thorium bromide.

13. A detector in accordance with claim 12 wherein the semiconductor material comprises crystalline $Cd_{1-(a+b)}Mn_aZn_bTe$, where a+b<1 and a and/or b may be zero.

14. A detector in accordance with claim 1 adapted to be used with a broad spectrum x-ray radiation source capable of producing broad spectrum emission over a range of energies in the range 1 to 160 keV.

15. A method of production of a detector comprising the steps of: providing an x-ray detector structure and defining a plurality of separately addressable regions disposed in an area array on a detection surface thereof for detecting incident x-ray radiation intensity thereon in use; and depositing on the detection surface of each separately addressable region a plurality of discrete filter layers each defining one of a plurality of sub-regions spaced across the detection surface of the separately addressable region, the filter layers of a given separately addressable region comprising discrete and different materials with discrete defined and spectroscopically spaced x-ray absorption edges, whereby each separately addressable region is divided into at least three sub-regions, wherein each region includes a filter layer selected with reference to a target material with a particular characteristic edge of interest such as to comprise a filter layer having a characteristic absorption edge below the edge of interest, a filter layer having a characteristic absorption edge above the edge of interest, and a filter layer having an absorption edge with the edge of interest, and wherein the detector structure is itself adapted to resolve incident radiation spectroscopically simultaneously across at least three energy bands within the spectrum of a source.

16. An apparatus for the inspection and characterisation of materials comprising:
a detector system composed of at least one detector device in accordance with claim 1; and
an x-ray source spaced therefrom to define an object scanning zone therebetween.

17. An apparatus in accordance with claim 16 wherein the source is selected to generate radiation across at least a major part of a range of 1 keV to 160 keV.

18. An apparatus in accordance with claim 16 further comprising an image generation module for generating an image dataset from transmitted intensity data incident upon the detector in use.

19. A method for the inspection and characterisation of materials comprising:
providing a detector system composed of at least one detector device in accordance with claim 1;
providing an x-ray source spaced therefrom to define an object scanning zone therebetween;
irradiating an object under test in the scanning zone;
comparing incident intensity from each sub-region of a separately addressable region of the detector; and
drawing inferences therefrom on the presence or absence of particular absorption edges in the material of the object under test, and hence about composition.

20. An method in accordance with claim 19 wherein the source is selected to generate radiation across at least a major part of a range of 1 keV to 160 keV.

21. A method in accordance with claim 19 further comprising the step of generation of an image from transmitted intensity data.

22. A method in accordance with claim 21 wherein an image is generated in which each separately addressable region comprises an image pixel and in which the image includes a representation of the inferences drawn from comparison of the intensity data from each sub-region.

23. A method in accordance with claim 22 wherein different identified absorption edge responses in a given separately addressable region are represented by presenting the pixel as different colors.

24. A method in accordance with claim 21 wherein the detector structure is selected such as to inherently resolve the source spectrum into a plurality of frequency bands within the spectrum of the source; and intensity data resolved spectroscopically across such plurality of frequency bands is allocated to generate a series of energy-differentiated images.

* * * * *